(12) United States Patent
Lee et al.

(10) Patent No.: US 9,271,916 B2
(45) Date of Patent: Mar. 1, 2016

(54) COMPOSITION FOR REDUCING SKIN WRINKLES INCLUDING PDE5 INHIBITOR

(71) Applicant: SK Chemicals Co., Ltd., Seongnam, Gyeonggi-Do (KR)

(72) Inventors: Soo-Min Lee, Seoul (KR); Sooheun Lee, Gyeonggi-Do (KR); Keun-Ho Ryu, Seoul (KR); Bong-Yong Lee, Seoul (KR); Jae-Sun Kim, Gyeonggi-Do (KR); Jung-Hoon Oh, Seoul (KR); Ye-Ji Jeon, Gyeonggi-Do (KR)

(73) Assignee: SK CHEMICALS CO., LTD., Seongnam, Gyeonggi-Do (KR)

( * ) Notice: Subject to any disclaimer, the term of this patent is extended or adjusted under 35 U.S.C. 154(b) by 61 days.

(21) Appl. No.: 14/201,137

(22) Filed: Mar. 7, 2014

(65) Prior Publication Data

US 2014/0187775 A1 Jul. 3, 2014

Related U.S. Application Data

(63) Continuation of application No. PCT/KR2012/007241, filed on Sep. 7, 2012.

(30) Foreign Application Priority Data

Sep. 9, 2011 (KR) .................. 10-2011-0091940

(51) Int. Cl.
*A61K 8/49* (2006.01)
*A61Q 19/00* (2006.01)
*A61Q 19/08* (2006.01)
*A61K 31/00* (2006.01)
*A61K 31/519* (2006.01)

(52) U.S. Cl.
CPC .............. *A61K 8/4953* (2013.01); *A61K 31/00* (2013.01); *A61K 31/519* (2013.01); *A61Q 19/00* (2013.01); *A61Q 19/08* (2013.01)

(58) Field of Classification Search
CPC ..... A61K 31/519; A61K 31/00; A61K 8/4953; A61Q 19/08; A61Q 19/00
USPC .......................................... 544/280
See application file for complete search history.

(56) References Cited

U.S. PATENT DOCUMENTS

| | | | | |
|---|---|---|---|---|
| 2003/0216407 A1* | 11/2003 | Butt et al. | ................ | 514/252.16 |
| 2008/0317679 A1* | 12/2008 | Tamarkin et al. | ............... | 424/45 |
| 2013/0053393 A1* | 2/2013 | Frangakis et al. | ....... | 514/252.16 |

FOREIGN PATENT DOCUMENTS

| | | |
|---|---|---|
| EP | 2556820 A2 | 2/2013 |
| KR | 10-2001-0020285 A | 3/2001 |
| KR | 10-2001-0083637 A | 9/2001 |
| WO | WO-2006/018088 A1 | 2/2006 |
| WO | WO-2010/019450 A2 | 2/2010 |

OTHER PUBLICATIONS

Haynes, W. M., ed., CRC handbook of chemistry and physics. CRC press, 2013, accessed online Feb. 10, 2015; excerpt p. 1-2.*
Cortijo, J. et al., "Effects of SCA40 on human isolated bronchus and human polymorphonuclear leukocytes: comparison with rolipram, SKF94120 and levcromakalim", British Journal of Pharmacology, 119, pp. 99-106 (1996).
Lee, J. et al., "Metabolism and excretion of 5-ethyl-2-{5-[4-(2-hydroxyethyl)piperazine-1-sulfonyl]-2-propoxyphenyl}-7-propl-3,5-dihydropyrrolo[3,3-d]-pyrimidin-4-one (SK3530) in rats", Rapid Commun. Mass. Spectrom., 21: 1139-1149 (2007).

* cited by examiner

*Primary Examiner* — Samantha Shterengarts
*Assistant Examiner* — Matt Mauro
(74) *Attorney, Agent, or Firm* — Mintz Levin Cohn Ferris Glovsky and Popeo, P.C.; Kongsik Kim; Elaine V. Morlock

(57) ABSTRACT

Disclosed is a composition effective in reducing skin wrinkles. The composition comprises a phosphodiesterase 5 (PDE5) inhibitor, preferably the compound of chemical formula 1, more preferably, mirodenafil as an active ingredient. Further disclosed is a method for reducing skin wrinkles using the composition.

3 Claims, 7 Drawing Sheets

DMSO : Dimethyl sulfoxide ## p<0.01, Significant difference from the normal control by Student t-test

* p<0.05, Significant difference from the negative control by Dunnett's t-test

** p<0.01, Significant difference from the negative control by Dunnett's t-test

COMPOSITION FOR REDUCING SKIN WRINKLES INCLUDING PDE5 INHIBITOR

CROSS-REFERENCE TO RELATED APPLICATION

This application is a continuation of International Application No. PCT/KR2012/007241 filed on Sep. 7, 2012, which claims priority to Korean Application No. 10-2011-0091940 filed on Sep. 9, 2011, which applications are incorporated herein by reference.

TECHNICAL FIELD

The present invention relates to a composition effective in reducing skin wrinkles and a method for reducing skin wrinkles using the composition.

BACKGROUND ART

Skin tends to be more susceptible to wrinkles than any other tissue because of frequent contact with various external stimuli. Particularly, facial skin is directly exposed to environmental factors such as sunlight, dry air and pollutants, and it begins to wrinkle earlier than other skin tissues.

The most characteristic change arising from the aging of skin tissues takes place in the skin matrix. Aging reduces the ability of skin fibroblasts in the dermis to create fiber and matrix components. Generally, a reduction in the amount of matrix leads to a decrease in skin thickness and deterioration of skin elasticity, causing the formation of wrinkles. That is, skin aging causes serious problems, such as elasticity loss, blood circulation disturbance and poor skin barrier function.

UV light exposure generates free radicals, reactive oxygen species (ROS), radical species derived from active carbonyl compounds, etc. in and on the skin. These active species are considered major causes of damage to skin cells. Further, the active species induce DNA damage and attack cell membrane structures, leaving age spots. Moreover, the attack of the active species causes loss of the functions of collagen and fibers to make the skin moist, soft, smooth and elastic, resulting in accelerated wrinkling. The administration of antioxidants for the removal of free radicals may also be helpful in reducing skin wrinkles. However, not all antioxidants exhibit satisfactory effects against skin wrinkling. Direct observation is desirable to better evaluate the effects of antioxidants on the reduction of skin wrinkles. Many drugs and cosmetics are currently being investigated for their potential to reduce skin wrinkles caused by external environmental factors and internal mechanisms.

SUMMARY

The present invention is designed to solve the problems of the prior art, and therefore it is an object of the present invention to provide a composition effective in reducing skin wrinkles. It is another object of the present invention to provide a method effective in reducing skin wrinkles.

An aspect of the present invention provides a composition for reducing skin wrinkles, comprising a phosphodiesterase 5 (PDE5) inhibitor, or a pharmaceutically acceptable salt, solvate or hydrate thereof as an active ingredient.

Another aspect of the present invention provides a method for reducing skin wrinkles, comprising administering or applying to a patient in need of treatment or improvement, i.e. skin wrinkle reduction, a therapeutically or cosmetically effective amount of at least one compound selected from compounds represented by the chemical formula 1, more preferably mirodenafil, or pharmaceutically acceptable salts, solvates and hydrates thereof.

The composition and method of the present invention are effective in reducing skin wrinkles.

BRIEF DESCRIPTION OF DRAWINGS

Other objects and aspects of the present invention will become apparent from the following description of embodiments with reference to the accompanying drawing in which.

DETAILED DESCRIPTION

Figure 1:
FIG. 1 shows photographs of a normal group (n=4) that was not irradiated with UV to induce wrinkles.

In one aspect, the present invention provide a composition for reducing skin wrinkles, comprising a phosphodiesterase 5 (PDE5) inhibitor, or a pharmaceutically acceptable salt, solvate or hydrate thereof as an active ingredient.

Phosphodiesterase refers collectively to a group of enzymes that cleave phosphodiester bonds in vivo. The PDE superfamily of enzymes is classified into 11 families, namely PDE1-PDE11, based on their amino acid sequences, substrate specificities, regulatory properties on vital reactions, pharmacological properties and tissue distribution. Of these, phosphodiesterase 5 inhibitors have been found to have a desirable influence on impotence, female sexual dysfunctions, angina pectoris, hypertension, heart failure and atherosclerosis. Particularly, phosphodiesterase 5 inhibitors are widely used in the treatment of impotence. However, the usefulness of PDE5 inhibitors, particularly those having specific structures, for the reduction of wrinkles has never been reported before. Thus, the present invention provides a novel use of PDE5 inhibitors as medicines or cosmetics for the reduction of skin wrinkles.

Preferably, compounds represented by the following chemical formula 1, or pharmaceutically acceptable salts, solvates or hydrates thereof are used as a PDE5 inhibitor according to the present invention.

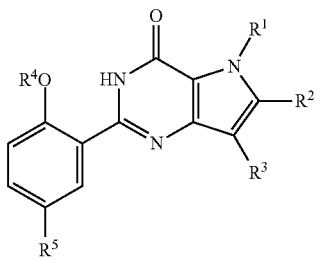

Chemical Formula 1

In the chemical formula 1, $R^1$ is H; $C_1$-$C_3$ alkyl optionally substituted with one or more fluoro atom(s); or $C_3$-$C_6$ cycloalkyl, $R^2$ is H; a halogen atom; $C_1$-$C_6$ alkyl optionally substituted with OH, $C_1$-$C_3$ alkoxy, $C_3$-$C_6$ cycloalkyl, or with one or more fluoro atom(s); $C_3$-$C_6$ cycloalkyl; $C_2$-$C_6$ alkenyl; or $C_2$-$C_6$ alkynyl, $R^3$ is H; $C_1$-$C_6$ alkyl optionally substituted with OH, $C_1$-$C_3$ alkoxy, $C_3$-$C_6$ cycloalkyl, or with one or more fluoro atoms; $C_3$-$C_6$ cycloalkyl; $C_2$-$C_6$ alkenyl; or $C_2$-$C_6$ alkynyl, $R^4$ is $C_1$-$C_6$ alkyl optionally substituted with $C_3$-$C_6$ cycloalkyl or with one or more fluoro atom(s); $C_2$-$C_6$ alkenyl; $C_2$-$C_6$ alkynyl; or $C_3$-$C_6$ cycloalkyl, $R^5$ is $SO_2NR^6R^7$; $NHSO_2NR^6R^7$; $NHCOCONR^6R^7$; $NHSO_2R^8$; $NHCOR^8$; or phenyl or heterocyclyl either of which is optionally substituted with one or more fluoro atom(s) or $C_1$-$C_3$ alkyl;

$R^6$ and $R^7$ are each independently H or $C_1$-$C_6$ alkyl optionally substituted with OH, $CO_2H$, $C_1$-$C_3$ alkoxy, $C_3$-$C_6$ cycloalkyl, or with one or more fluoro atom(s); or together with the nitrogen atom to which they are attached form either a mono-cyclic ring such as imidazole, aziridene (aziridine), azeridine (azetidine), pyrrolidine, piperidine, morpholine, piperazine and homopiperazine, or a bicyclic ring such as 2,5-diazabicyclo[2.2.1]heptane and 3,7-diazabicyclo[3.3.0]octane, wherein said group is optionally substituted with $R^9$, $R^8$ is $C_1$-$C_3$ alkyl optionally substituted with one or more fluoro atom(s); or $C_3$-$C_7$ cycloalkyl;

$R^9$ is $C_1$-$C_6$ alkyl optionally substituted with one or more halide atom(s), OH, $C_1$-$C_3$ alkoxy which is optionally substituted with one or more fluoro atom(s), $CO_2R^{10}$, $NR^{11}R^{12}$, $C=NR(NR^{14}R^{15})$, or with a tetrazole group which is optionally substituted with $C_1$-$C_3$ alkyl; or one or more nitrogen containing heteroaryl group which is optionally substituted with one or more fluoro atom(s), $R^{10}$ is H; or $C_1$-$C_4$ alkyl optionally substituted with OH, $NR^{11}R^{12}$, one or more fluoro atom(s), or with a nitrogen containing heterocyclic ring such as pyrrolidine, piperidine, piperazine, morpholine, pyrrole, and imidazole wherein nitrogen atom is directly bound to $C_1$-$C_4$ alkyl, $R^{11}$ and $R^{12}$ are each independently H or $C_1$-$C_4$ alkyl, $R^{13}$ is H; $C_1$-$C_4$ alkyl optionally substituted with one or more fluoro atoms; or $C_1$-$C_6$ cycloalkyl, $R^{14}$ and $R^{15}$ are each independently H or $C_1$-$C_4$ alkyl optionally substituted with one or more fluoro atoms; $C_3$-$C_6$ cycloalkyl; or together with the nitrogen atom to which they are attached form a pyrrolidinyl, piperidino, morpholino, piperazinyl, or homopiperazinyl group wherein said group is optionally substituted with $C_1$-$C_3$ alkyl.

Preferably, in the chemical formula 1, $R^1$ is H; methyl; or ethyl, $R^2$ is H; methyl; or a halogen atom, $R^3$ is $C_1$-$C_4$ alkyl optionally substituted with one or more fluoro atom(s), $R^4$ is ethyl; n-propyl; or allyl, $R^5$ is $SO_2NR^6R^7$ or $NHSO_2R^8$, $R^6$ and $R^7$ taken together with the nitrogen atom to which they are attached form a piperidino, piperazinyl or homopiperazinyl group wherein said group is substituted with $R^9$, $R^8$ is methyl, $R^9$ is $C_1$-$C_4$ alkyl optionally substituted with one or more halide atom(s), OH, $CO_2R^{10}$, or with a tetrazole group which is optionally substituted with $C_1$-$C_3$ alkyl, and $R^{10}$ is H.

More preferably, examples of PDE5 inhibitors suitable for use in the composition of the present invention include 2-(2-ethoxy-5-(4-methy)piperazin-1-ylsulfonyl)phenyl)-5-methyl-7-n-propyl-3,5-dihydro-4H-pyrrolo[3,2-d]pyrimidin-4-one;

2-(5-(4-methylpiperazin-1-ylsulfonyl)-2-n-propoxyphenyl)-5-methyl-7-n-propyl-3,5-dihydro-4,1-pyrrolo[3,2-d]pyrimidin-4-one;

2-(2-ethoxy-5-(4-n-propylpiperazin-1-ylsulfonyl)phenyl)-5-methyl-7-n-propyl-3,5-dihydro-4H-pyrrolo[3,2-d]pyrimidin-4-one;

2-(2-ethoxy-5-(4-isopropylpiperazin-1-ylsulfonyl)phenyl)-5-methyl-7-n-propyl-3,5-dihydro-4H-pyrrolo[3,2-d]pyrimidin-4-one;

2-(2-ethoxy-5-(4-(2-fluoroethyl)piperazin-1-ylsulfonyl)phenyl)-5-methyl-7-n-propyl-3,5-dihydro-4H-pyrrolo[3,2-d]pyrimidin-4-one;

2-(5-(4-(2-fluoroethyl)piperazin-1-ylsulfonyl)-2-n-propoxyphenyl)-5-methyl-7-n-propyl-3,5-dihydro-4H-pyrrolo[3,2-d]pyrimidin-4-one;

2-(2-ethoxy-5-(4-(3-fluoropropyl)piperazin-1-ylsulfonyl)phenyl)-5-methyl-7-n-propyl-3,5-dihydro-4H-pyrrolo[3,2-d]pyrimidin-4-one;

2-(2-ethoxy-5-(4-(3-fluoropropyl)piperazin-1-ylsulfonyl)phenyl)-7-ethyl-5-methyl-3,5-dihydro-4H-pyrrolo[3,2-d]pyrimidin-4-one;

2-(2-ethoxy-5-(4-(3-fluoropropyl)piperazin-1-ylsulfonyl)phenyl)-7-(3-fluoropropyl)-5-methyl-3,5-dihydro-4H-pyrrolo[3,2-d]pyrimidin-4-one;

7-cyclopropylmethyl-2-(2-ethoxy-5-(4-(3-fluoropropyl)piperazin-1-ylsulfonyl)phenyl)-5-methyl-3,5-dihydro-4H-pyrrolo[3,2-d]pyrimidin-4-one;

2-(2-ethoxy-5-(4-(3-fluoropropyl)piperazin-1-ylsulfonyl)phenyl)-5-ethyl-7-ethyl-3,5-dihydro-4H-pyrrolo[3,2-d]pyrimidin-4-one;

2-(2-ethoxy-5-(4-(3-fluoropropyl)piperazin-1-ylsulfonyl)phenyl)-5-ethyl-7-n-propyl-3,5-dihydro-4H-pyrrolo[3,2-d]pyrimidin-4-one;

2-(2-ethoxy-5-(4-isopropylpiperazin-1-ylsulfonyl)phenyl)-5-ethyl-7-n-propyl-3,5-dihydro-4H-pyrrolo[3,2-d]pyrimidin-4-one;

2-(2-ethoxy-5-(4-(3-fluoropropyl)piperazin-1-ylsulfonyl)phenyl)-5-ethyl-7-n-propyl-3,5-dihydro-4H-pyrrolo[3,2-d]pyrimidin-4-one;

2-(2-ethoxy-5-(4-(2-hydroxyethyl)piperazin-1-ylsulfonyl)phenyl)-5-ethyl-7-n-propyl-3,5-dihydro-4H-pyrrolo[3,2-d]pyrimidin-4-one;

2-(2-ethoxy-5-(4-ethylpiperazin-1-ylsulfonyl)phenyl)-5-ethyl-7-(3-fluoropropyl)-3,5-d-dihydro-4H-pyrrolo[3,2-d]pyrimidin-4-one;

2-(5-(4-ethylpiperazin-1-ylsulfonyl)-2-n-propoxyphenyl)-5-ethyl-7-(3-fluoropropyl)-3-5-dihydro-4H-pyrrolo[3,2-d]pyrimidin-4-one;

2-(2-ethoxy-5-(4-isopropylpiperazin-1-ylsulfonyl)phenyl)-5-ethyl-7-(3-fluoropropyl)-3,5-dihydro-4H-pyrrolo[3,2-d]pyrimidin-4-one;

2-(2-ethoxy-5-(4-(3-fluoropropyl)piperazin-1-ylsulfonyl)
phenyl)-5-ethyl-7-(3-fluoropropyl)-3,5-dihydro-4H-pyr-
rolo[3,2-d]pyrimidin-4-one;

2-(5-(4-(3-fluoropropyl)piperazin-1-ylsulfonyl)-2-n-pro-
poxyphenyl)-5-ethyl-7-(3-fluoropropyl)-3,5-dihydro-4H-
pyrrolo[3,2-d]pyrimidin-4-one;

2-(2-ethoxy-5-(4-(2-hydroxyethyl)piperazin-1-ylsulfonyl)
phenyl)-5-ethyl-7-(3-fluoropropyl)-3,5-dihydro-4H-pyr-
rolo[3,2-d]pyrimidin-4-one;

2-(5-(4-(2-hydroxyethyl)piperazin-1-ylsulfonyl)-2-n-pro-
poxyphenyl)-5-ethyl-7-(3-fluoropropyl)-3,5-dihydro-4H-
pyrrolo[3,2-d]pyrimidin-4-one;

2-(5-(4-(3-hydroxypropyl)piperazin-1-ylsulfonyl)-2-n-pro-
poxyphenyl)-5-ethyl-7-(3-fluoropropyl)-3,5-dihydro-4H-
pyrrolo[3,2-d]pyrimidin-4-one;

2-(5-(4-(2-hydroxyethyl)piperazin-1-ylsulfonyl)-2-n-pro-
poxyphenyl)-5-ethyl-7-n-propyl-3,5-dihydro-4H-pyrrolo
[3,2-d]pyrimidin-4-one;

2-(5-(4-(3-fluoropropyl)piperazin-1-ylsulfonyl)-2-n-pro-
poxyphenyl)-5-methyl-7-n-propyl-3,5-dihydro-4H-pyr-
rolo[3,2-d]pyrimidin-4-one;

2-(2-ethoxy-5-(4-(2-hydroxyethyl)piperazin-1-ylsulfonyl)
phenyl)-5-methyl-7-n-propyl-3,5-dihydro-4H-pyrrolo[3,
2-d]pyrimidin-4-one;

2-(5-(4-(2-hydroxyethyl)piperazin-1-ylsulfonyl)-2-n-pro-
poxyphenyl)-5-methyl-7-n-propyl-3,5-dihydro-4H-pyr-
rolo[3,2-d]pyrimidin-4-one;

2-(5-(2-ethoxy-4-(3-hydroxypropyl)piperazin-1-ylsulfonyl)
phenyl)-5-methyl-7-n-propyl-3,5-dihydro-4H-pyrrolo[3,
2-d]pyrimidin-4-one;

2-(5-(4-(3-hydroxypropyl)piperazin-1-ylsulfonyl)-2-n-pro-
poxyphenyl)-5-methyl-7-n-propyl-3,5-dihydro-4H-pyr-
rolo[3,2-d]pyrimidin-4-one;

2-(2-ethoxy-5-(4-(hydroxycarbonylmethyl)piperidin-1-yl-
sulfonyl)phenyl)-5-methyl-7-n-propyl-3,5-dihydro-4H-
pyrrolo[3,2 -d]pyrimidin-4-one;

2-(5-(4-(hydroxycarbonylmethyl)piperidin-1-ylsulfonyl)-2-
n-propoxyphenyl)-5-methyl-7-n-propyl-3,5-dihydro-4H-
pyrrolo[3,2-d]pyrimidin-4-one;

2-(2-ethoxy-5-(4-(2-hydroxycarbonylethyl)piperidin-1-yl-
sulfonyl)phenyl)-5-methyl-7-n-propyl-3,5-dihydro-4H-
pyrrolo[3,2-d]pyrimidin-4-one;

2-(5-(4-(2-hydroxycarbonylethyl)piperidin-1-ylsulfonyl)-2-
n-propoxyphenyl)-5-methyl-7-n-propyl-3,5-dihydro-4H-
pyrrolo[3,2-d]pyrimidin-4-one;

2-(2-ethoxy-5-(4-(1H-tetrazol-5-ylmethyl)piperazin-1-yl-
sulfonyl)phenyl)-5-methyl-7-n-propyl-3,5-dihydro-4H-
pyrrolo[3,2-d]pyrimidin-4-one;

5-methyl-2-(2-n-propoxy-5-(4-(2-(1H-tetrazol-5-yl)ethyl)
piperazin-1-ylsulfonyl)phenyl)-7-n-propyl-3,5-dihydro-
4H-pyrrolo[3,2-d]pyrimidin-4-one;

2-(2-ethoxy-5-(4-(1H-tetrazol-5-ylmethyl)piperidin-1-yl-
sulfonyl)phenyl)-5-methyl-7-n-propyl-3,5-dihydro-4H-
pyrrolo[3,2-d]pyrimidin-4-one;

5-methyl-2-(2-n-propoxy-5-(4-(1H-tetrazol-5-ylmethyl)pip-
eridin-1-ylsulfonyl)phenyl)-7-n-propyl-3,5-dihydro-4H-
pyrrolo[3,2-d]pyrimidin-4-one;

and pharmaceutically acceptable salts, solvates and hydrates thereof.

Mirodenafil or a pharmaceutically acceptable salt, solvate or hydrate thereof is the most preferred PDE5 inhibitor as an active ingredient of the composition according to the present invention.

The above-mentioned PDE5 inhibitors can be prepared by the methods disclosed in, for example, U.S. Pat. No. 6,962,911, which is incorporated herein by reference in its entirety.

It is assumed that the PDE5 inhibitor used in the composition of the present invention acts on PDE5 in the skin to relax muscles and inhibits shrinkage of the relaxed muscles to effectively reduce wrinkles in a manner similar to the mechanism of BOTOX, which is currently used to reduce skin wrinkles. However, the present invention is not limited to the probable mechanism.

Some of the PDE5 inhibitors (hereinafter, also referred to simply as "compounds") can be administered in the form of pharmaceutically acceptable salts. The term "pharmaceutically acceptable salts" refers to salts that are prepared using nontoxic or relatively less toxic acids or bases. When the compounds are relatively acidic, base addition salts can be obtained by bringing neutral forms of such compounds into contact with a sufficient amount of the desired base in an inert solvent. Examples of such pharmaceutically acceptable base addition salts include, but are not limited to, lithium, sodium, potassium, calcium, ammonium, magnesium and organic amine salts. When the compounds are relatively basic, acid addition salts can be obtained by bringing neutral forms of such compounds into contact with a sufficient amount of the desired acid in an inert solvent. Examples of such pharmaceutically acceptable acid addition salts include, but are not limited to, propionic acid, isobutyric acid, oxalic acid, malic acid, malonic acid, benzoic acid, succinic acid, suberic acid, fumaric acid, mandelic acid, phthalic acid, benzenesulfonic acid, p-tolylsulfonic acid, citric acid, tartaric acid, methanesulfonic acid, hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydroiodic acid, and phosphorous acid. Other examples include, but are not limited to, salts of amino acids, such as arginate, and analogs of organic acids, such as glucuronic acid and galacturonic acid.

The compounds may exist in unsolvated forms as well as solvated forms, including hydrated forms, depending on their characteristics. The compounds may exist in crystalline or amorphous forms. Such all physical forms are encompassed within the scope of the present invention.

The compounds may exist as racemates, enantiomers, diastereomers, geometric isomers, etc. due to the presence of one or more asymmetric carbon atoms as chiral centers or one or more double bonds. Some of the compounds may also exist in tautomeric forms. These structures are also encompassed within the scope of the present invention.

The composition of the present invention can be prepared into medicines, functional foods and cosmetics. Such medicines, functional foods and cosmetics may include one or more pharmaceutically acceptable excipients or additives. The composition of the present invention may be administered alone or in combination with at least one pharmaceutically acceptable carrier or excipient, in either single or multiple doses.

The medicines, functional foods and cosmetics may be solid, liquid or semi-solid preparations. Non-limiting examples of the solid preparations include powders, granules, tablets, capsules and suppositories. The solid preparations may include suitable diluents, flavors, binders, preservatives, disintegrants, lubricants, fillers, etc. Non-limiting examples of the liquid preparations include solutions, such as aqueous solutions and propylene glycol solutions, suspensions, and emulsions. The liquid preparations may include suitable colorants, flavors, stabilizers and thickeners. Non-limiting examples of the semi-solid preparations include creams, lotions, emulsions and liniments. The semi-solid preparations may include suitable colorants, flavors, stabilizers, thickeners and surfactants. In view of the purpose of reducing skin wrinkles, which is to be achieved by the composition of the present invention, it is preferred to directly apply the composition topically to the skin because topical application reduces the possibility of side effects at other sites of the body. Therefore, it is more preferred that the composition of the present invention be formulated into semi-solid preparations.

For example, a powder may be prepared by simply mixing the compound with a suitable pharmaceutically acceptable excipient such as lactose, starch or microcrystalline cellulose. A granule may be prepared by mixing the compound, a suitable pharmaceutically acceptable excipient and a suitable pharmaceutically acceptable binder such as polyvinyl pyrrolidone or hydroxypropyl cellulose, and granulating the mixture using a suitable solvent such as water, ethanol or isopropanol (wet granulation) or by a compressive force (dry granulation). A tablet may be prepared by mixing the granule with a suitable pharmaceutically acceptable lubricant such as magnesium stearate, and compacting the mixture using a suitable tableting machine.

The composition of the present invention is preferably prepared into a general skin cosmetic formulation because it is preferred to apply the composition topically to the skin, as mentioned earlier. Specifically, the composition of the present invention can be prepared into lotions, essences, cosmetic oils, creams, powders, packs, foundations, make-up bases and cosmetic sticks. The composition of the present invention can be applied to a variety of states, such as liquids, creams, pastes and solids, which can be prepared by methods commonly known in the field of cosmetics.

For example, a lotion may be prepared by dispersing a carbomer in purified water with stirring, adding butylene glycol, glycerin and PEG-1500 to the dispersion, and mixing the mixture with a solution of polyoxyethylene cured castor oil, triethanol, a preservative and the compound in a suitable solvent such as ethanol. Alternatively, a lotion may be prepared by dissolving cetearyl alcohol, glyceryl stearate/PEG-100 stearate, Polysorbate 60, sorbitan sesquioleate, cetyl octanoate and squalene at a temperature of about 70 C.°, emulsifying the solution in a dispersion of butylene glycol, magnesium aluminum silicate, xanthan gum and a preservative in purified water at 70 C.°, cooling the emulsion, adding the emulsion to a solution of the compound in a suitable solvent or component, stirring the mixture, and cooling the mixture to room temperature.

There is no restriction on the route of administration of the composition according to the present invention. For example, the composition of the present invention may be administered orally, by injection (for example, intramuscular injection, intraperitoneal injection, intravenous injection, infusion, subcutaneous injection or implantation), by inhalation, nasally, intravaginally, rectally, sublingually, transdermally, topically, etc. depending on the type of diseases and the condition of subjects to treated. The composition of the present invention may be prepared into an appropriate unit dosage form comprising at least one known non-toxic, pharmaceutically acceptable carrier, adjuvant or vehicle, depending on the desired route of administration. The composition of the present invention may also be prepared into a depot formulation from which the active ingredient can be continuously released for a certain period of time, which is also encompassed within the scope of the present invention. In view of the purpose of reducing skin wrinkles, which is to be achieved by the composition of the present invention, a preparation for topical application is most preferred in because the composition can be directly applied to the skin.

In order to achieve the purpose of the present invention, the PDE5 inhibitor may be administered at a dose of about 0.1 mg/kg to about 200 mg/kg daily. The daily dose for the PDE5 inhibitor is preferably from about 0.5 mg/kg to about 100 mg/kg. The dose of the PDE5 inhibitor may be varied depending on the conditions of patients, e.g., age, sex and body weight, and the severity of the particular condition to be treated. For convenience of administration, if needed, the daily dose of the PDE5 inhibitor can be administered in a single dose or in divided doses. When it is intended to directly administer the compound topically to the skin, the daily dose is preferably in the range of about 0.05 mg/cm$^2$ of skin area to 50 mg/cm$^2$ of skin area, but is not limited to this range.

In another aspect, the present invention provides a method for reducing skin wrinkles, comprising administering or applying to a patient in need of treatment or improvement, i.e. skin wrinkle reduction, a therapeutically or cosmetically effective amount of at least one compound selected from compounds represented by the chemical formula 1, more preferably mirodenafil, or pharmaceutically acceptable salts, solvates and hydrates thereof.

EXAMPLES

Hereinafter, the above-described and other embodiments of the present invention will be described in detail with reference to the following examples and the accompanying drawings. The embodiments of the present invention, however, may take several other forms, and the scope of the invention should not be construed as being limited to the following examples. The embodiments of the present invention are provided to more fully explain the present invention to those having ordinary knowledge in the art to which the present invention belongs.

Example 1

Determination of Expression of PDE5 in the Skin

In this example, the expression of PDE5 in some skin tissues was determined in order to examine the ability of PDE5 inhibitors to reduce facial skin wrinkles.

Kidney and prostate tissues, where PDE5 is known to be expressed, and skin tissues were excised from male Sprague-Dawley (SD) rats, aged 7 weeks. The expression of PDE5 in tissues was confirmed by the following procedure. First, each of the tissues was cut into a piece having a weight of approximately 100 mg. Thereafter, the tissue was subjected to homogenization and RNA extraction. The RNA was quantified. 1 μg of the RNA was used for cDNA construction. The expression of PDE5 in the tissue was confirmed by real-time PCR analysis of the cDNA. β-actin was used as a control. 5'-TTGACGGATCTGGAGACGCT-3' (forward primer) and 5'-CACCACGATGGTCCAAATCA-3' (reverse primer) were used as primers for PDE5. 5'-ACCTTCAACAC-CCAGCCA-3' (forward primer) and 5'-CAGTGGTAC-GACCAGAGGCA-3' (reverse primer) were used as primers for β-actin (see BJU INTERNATIONAL 2006 (98) 1259-1263). The relative expression levels of PDE5 in the different tissues are shown in Table 1. Data shown in Table 1 are presented as mean±standard deviation.

TABLE 1

| Kidney | Prostate | Skin |
|---|---|---|
| 0.5897 ± 0.2638 | 1.2174 ± 0.3857 | 1.4641 ± 0.3498 |

As can be seen from the results in Table 1, PDE5 was highly expressed in the skin tissues, similarly to in the kidney and prostate tissues, where PDE5 is known to be expressed at an appreciable level. These results reveal that the compounds inhibit PDE5 in the skin and can have an influence to some extent on the skin.

Example 2

Evaluation of Wrinkle Reduction Effects in the Skin

An examination was made as to whether the PDE5 inhibitors can substantially reduce skin wrinkles of animal models. Hairless mice, aged 7 weeks, were irradiated with UVB (290-320 nm, 312 nm) to induce wrinkles. The compound or the control was applied to each mouse and its influence on the induced wrinkles was evaluated.

More specifically, the mice were irradiated with 60 mJ/cm$^2$ (1 minimal edemal dose (MED)) for 3 days weekly during the first and second week after wrinkling, 120 mJ/cm$^2$ (2 MED) for 3 days during the third week after wrinkling, 180 mJ/cm$^2$ (3 MED) for 3 days during the fourth week after wrinkling, 240 mJ/cm$^2$ (4 MED) for 3 days weekly during the fifth to eighth week after wrinkling, and 240 mJ/cm$^2$ (4 MED) for 5 days weekly during the ninth to fifteenth week after wrinkling. During the sixteenth and seventeenth week after wrinkling, about 0.5 ml of squalene-OOH, an oxidation product of squalene by UV irradiation, was applied once using a brush to induce deeper wrinkles. Thereafter, the compound or the control was applied to each mouse twice daily for 14 days. Photographs were taken of the skins and are shown in FIGS. 1-5.

FIG. 1 shows photographs of the normal group (n=4) that was not irradiated with UV to induce wrinkles. Some shallow wrinkles were naturally formed in the normal group with increasing age of the mice, but the wrinkles are thin and not deep.

Figure 2:
FIG. 2 shows photographs of a negative control (n=6) that was irradiated with UV to induce wrinkles and treated with a medium (20% EtOH, 30% DW, 50% PEG) only without administration of any active ingredient.

FIG. 2 shows photographs of the negative control (n=6) after UV irradiation to induce wrinkles and treated with a medium (20% EtOH, 30% DW, 50% PEG) only for 2 weeks without administration of any active ingredient. Many deep wrinkles were observed in the negative control.

Figure 3:
FIG. 3 shows photographs of a group (n=7) treated with 10 mM (about 5%) mirodenafil free base after wrinkles were induced.

FIG. 3 shows photographs of the group (n=7) treated with 10 mM (about 5%) mirodenafil free base, a preferable PDE5 inhibitor, after wrinkles were induced. Wrinkle reduction was observed in the group. The skins of the group gradually became clean.

Figure 4:
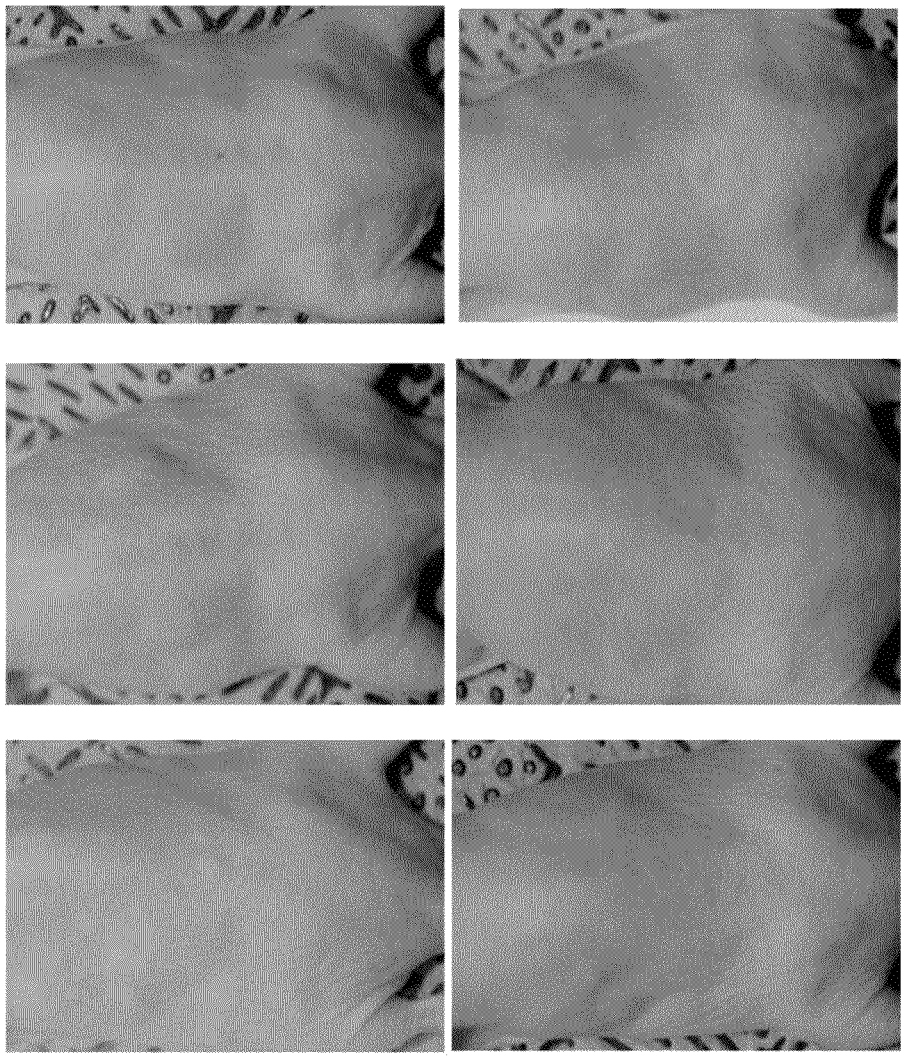
FIG. 4 shows photographs of a group (n=6) treated with 10 mM (about 5%) mirodenafil 2HCl after wrinkles were induced.

FIG. 4 shows photographs of the group (n=6) treated with 10 mM (about 5%) mirodenafil 2HCl, a preferable PDE5 inhibitor, after wrinkles were induced. Wrinkle reduction was observed in the group. The skins of the group gradually became clean.

Figure 5:
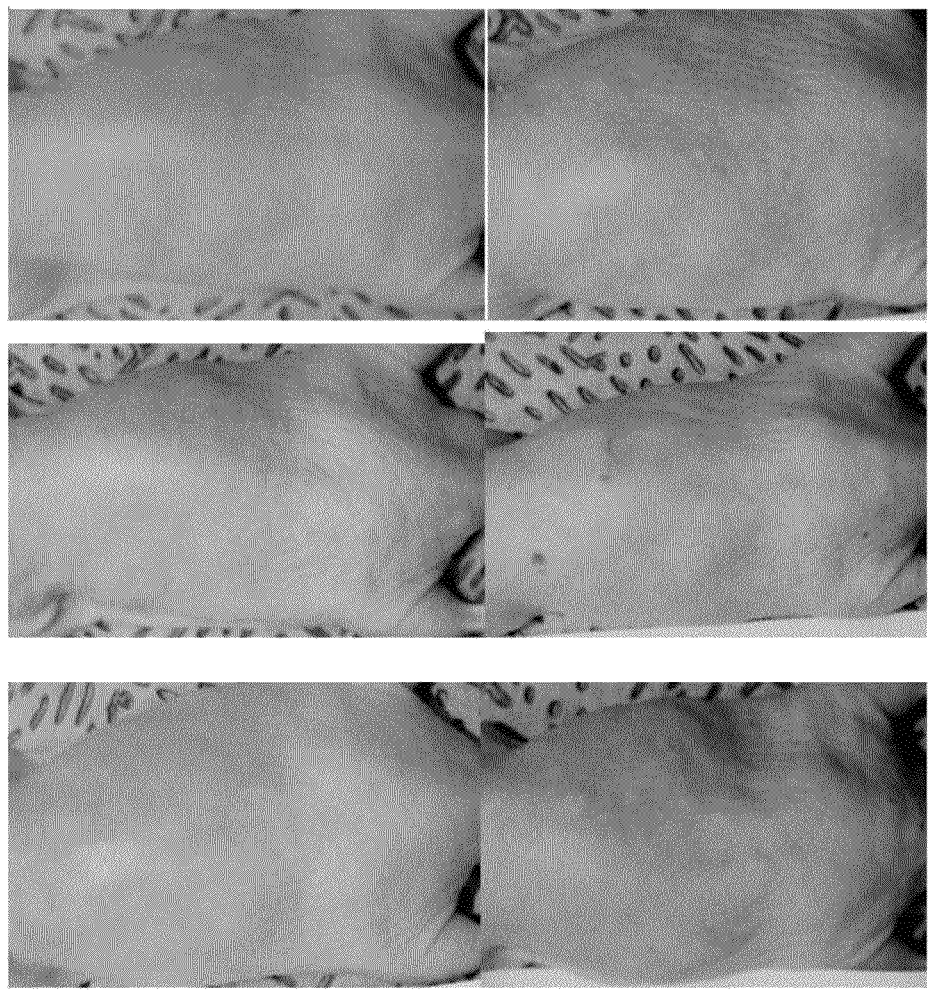
FIG. 5 shows photographs of a positive control (n=6) treated with 0.05% retinoic acid.

FIG. 5 shows photographs of the positive control (n=6) treated with 0.05% retinoic acid. Cornified layers were formed and continuously peeled, and thus the frequency of applications of retinoic acid changed from twice to once daily. However, continuous formation and peeling of cornified layers were still observed, even though the degree of the peeling decreased. Slight wrinkle reduction was observed, but the speed of cornification was faster than that of wrinkle reduction.

Example 3

Evaluation of Expedited Collagen Production

Effects by mirodenafil hydrochloride, test compound, on production of type I collagen was evaluated with normal human dermal fibroblasts.

Cell line 7F3802 was used as a normal human dermal fibroblast (hereinafter, 'NHDF'). Frozen NHDF was thawed and subcultured, and passages 5 to 7 were used for this test.

L-Ascorbic acid (Sigma-Aldrich Co., U.S.A.) was used as a positive control because there are lots of comparative experimental data using l-ascorbic acid. L-Ascorbic acid has been reported to be effective in acceleration of collagen production when evaluating with fibroblasts. DMSO (Dimethyl sulfoxide) was used as a diluent.

0.01 mL of aliquot was taken from 10 mM of mirodenafil hydrochloride stock solution, and 9.99 mL of DMSO was added to the aliquot to make 10,000 nM of sample. This sample was additionally diluted to 1,000 nM of concentration right before being used. 10,000 nM and 1,000 nM of solutions were diluted 100 times with serum-free medium to 10 and 100 nM, respectively, right before being applied.

For making a positive control, 20,000 µM (3.522 mg/mL) of l-ascorbic acid was prepared by dissolving it with serum-free medium, and then the solution was diluted to 200 µM.

Two cell culture media were used in this experiment. Complete medium consisting of FBS (fetal bovine serum), Penicillin-Streptomycin (10,000 U/mL of penicillin and 10,000 ug of streptomycin) and DMEM/F12 (dulbecco's modified eagle's medium/F12) was used during subculture before test compound was applied, and then serum-free medium consisting of Penicillin-Streptomycin and DMEM (dulbecco's modified eagle's medium) was used.

Pre-treatment (cell culture and treatment of test compound) was performed as follows: After culturing in complete medium, 400 µl of NHDF was seeded into 48-well plates ($1 \times 10^5$ cells/400 µl/well), and cultured at a condition of 37° C. and 5% $CO_2$ incubator (MCO-20AIC, Sanyo, Japan) for 24 hours. After culture was completed, the remaining media were removed from each well. 500 µl of D-PBS (D-phosphate buffered saline) was added to each well to wash wells. 800 µL of test compound solution or positive control solution was added to each well. 800 µL of serum-free medium comprising DMSO was added to negative control well. Then wells were incubated in the same condition for 48 hours. After culture was completed, medium of each well was collected and centrifuged (25° C., 3000 rpm, 10 min.). Supernatant liquid was used for determining the content of procollagen type I. 1 mL of D-PBS was added for washing to the plate, and 300 µl of cell lysis buffer (Lot No.: 41, Cell signaling Technology, U.S.A) was added to each well. Plate was stored in a deep freezer (−70° C., DFU-657CL, Operon, Korea) for 2 hours to make cells frozen, and then cells were thawed at room temperature. This procedure was repeated two times to lyse cells. Cell lysate was collected and centrifuged (Micro 17TR, HANIL SCIENCE INDUSTRIAL. Korea., 4° C., 13000 rpm, 30 min.), and then supernatant liquid was used for determining the content of total protein.

BCA protein assay kit (Lot No.: KK140637, Pierce Biotechnology Inc., USA) was used for total protein analysis, and procollagen type I C-peptide EIA kit (Lot No.: AB01520C, Takara Bio Inc., Japan) was used for Procollagen type I analysis.

The contents of procollagen type I in wells to which negative control, test compound or positive control was added were divided by the content of total protein. The adjusted content of procollagen type I was used to calculate "Synthesis rate of procollagen type I" with the following equation. This test was repeated three times.

Synthesis rate of procollagen type I (%)=$(B-A)/B \times 100$

Figure 6:
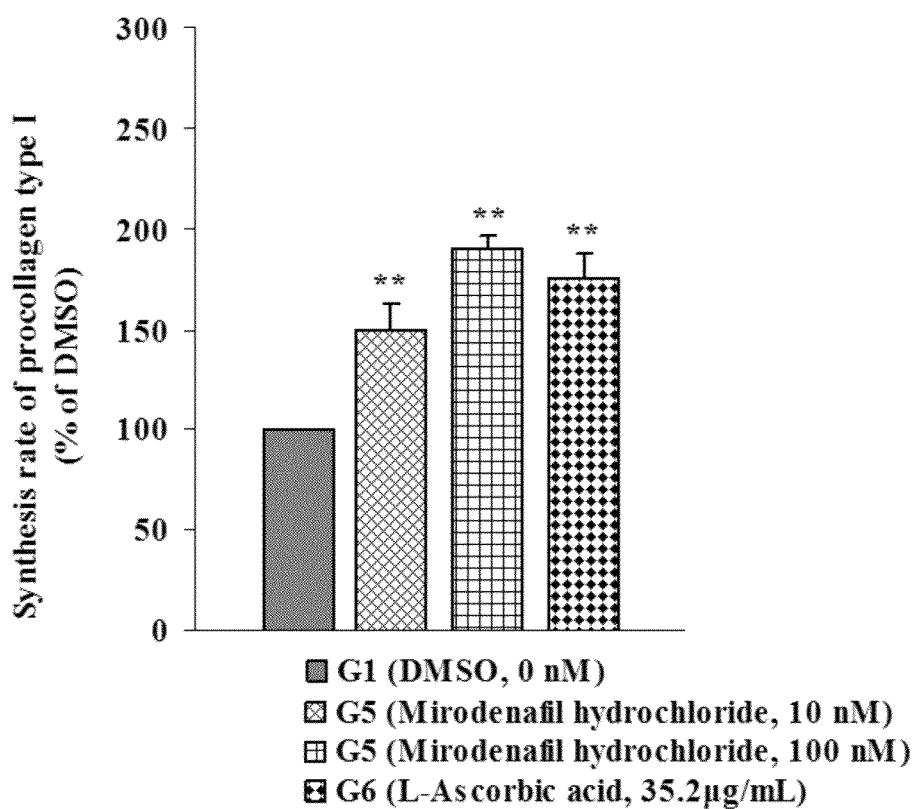
FIG. 6 graphically shows effects of mirodenafil hydrochloride on the production of type I procollagen in human skin fibroblast.

A: Procollagen type I amount of test substance or positive control
B: Procollagen type I amount of negative control Results were shown in FIG. 6. As shown in FIG. 6, synthesis rates of procollagen type I of 10 and 100 nM of mirodenafil hydrochloride showed statistically significant increase (p<0.01: 10 nM; 149.7±12.4%, 100 nM; 189.8±6.4%) compared to the negative control (100.0±0.0%). Synthesis rates of procollagen type I of 35.2 μg/mL (200 μM) of positive control also showed statistically significant increase (p<0.01: 35.2 μg/mL; 175.7±11.5%) compared to the negative control.

Example 4

Evaluation of Inhibited MMP-1 Expression

Effects by mirodenafil hydrochloride, test compound, on inhibition of matrix metalloproteinase-1 (MMP-1) expression was evaluated with normal human dermal fibroblasts.

(−)Epigallocatechin gallate (EGCG) (Sigma-Aldrich Co., U.S.A.) was used as a positive control because there are lots of comparative experimental data using the EGCG. EGCG has been reported to be effective in inhibition of MMP-1 expression when evaluating with fibroblasts. DMSO (Dimethyl sulfoxide) was used as a diluent.

0.01 mL of aliquot was taken from 10 mM of mirodenafil hydrochloride stock solution, and 9.99 mL of DMSO was added to the aliquot to make 10,000 nM of sample. This sample was additionally diluted to 1,000 nM of concentration right before being used. 10,000 nM and 1,000 nM of solutions were diluted 100 times with serum-free medium to 10 and 100 nM, respectively, right before being applied.

For making a positive control, 10,000 μM (4.584 mg/mL) of EGCG was prepared by dissolving it with serum-free medium, and then the solution was diluted to 10 μM (0.0046 mg/mL).

BCA protein assay kit (Lot No.: KK140637, Pierce Biotechnology Inc., USA) was used for total protein analysis, and matrix metalloproteinase-1 (MMP-1), human, biotrak ELISA system kit (Lot No.: 398061, GE Healthcare, UK) was used for MMP-1 analysis.

The contents of MMP-1 in wells to which negative control, test compound or positive control was added were divided by the content of total protein. The adjusted content of MMP-1 was used to calculate "Inhibition rate of MMP-1 expression" with the following equation. This test was repeated three times.

Inhibition rate of MMP-1 expression (%)=$A/B \times 100$

A: MMP-1 amount of sample or positive control
B: MMP-1 amount of negative control The other materials and methods which were not mentioned in detail were similar to those of Example 3.

Figure 7:
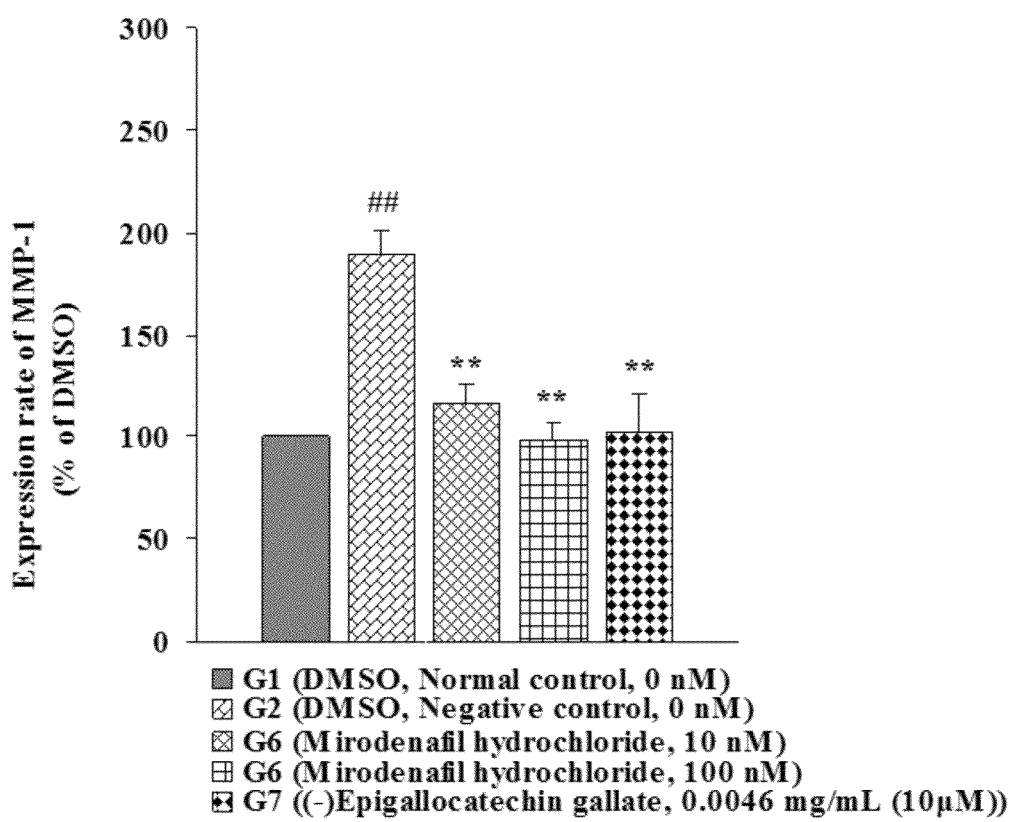
FIG. 7 graphically shows effects of mirodenafil hydrochloride on the inhibition of MMP-1 expression in human skin fibroblast.

Results were shown in FIG. 7. Inhibition rates of MMP-1 expression of 10 and 100 nM of mirodenafil hydrochloride were 115.8±9.1% and 97.9±8.5%, respectively and significantly (p<0.01) increased compared to the negative control (189.7±10.9%). In addition, inhibition rate of MMP-1 expression of 0.0046 mg/mL (10 μM) of positive control was 102.3±18.7%, which was significantly (p<0.01) low compared to the negative control (189.7±10.9%).

The present invention has been described in detail. However, it should be understood that the detailed description and specific examples, while indicating preferred embodiments of the invention, are given by way of illustration only, since various changes and modifications within the spirit and scope of the invention will become apparent to those skilled in the art from this detailed description.

What is claimed is:

1. A method for reducing skin wrinkles in a subject through stimulatory effects on collagen production, the method comprising administering to a subject in need thereof a therapeutically effective amount of phosphodiesterase 5 (PDE5) inhibitor or a pharmaceutically acceptable salt, solvate or hydrate thereof,
wherein the PDE5 inhibitor is a compound represented by the following chemical formula 1, or a pharmaceutically acceptable salt, solvate or hydrate, Chemical Formula 1

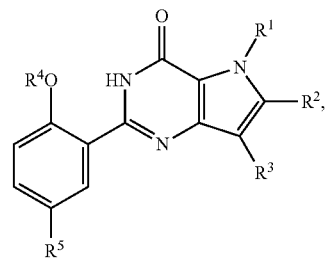

wherein
$R^1$ is H; $C_1$-$C_3$ alkyl optionally substituted with one or more fluoro atom(s); or $C_3$-$C_6$ cycloalkyl,
$R^2$ is H; a halogen atom; $C_1$-$C_6$ alkyl optionally substituted with OH, $C_1$-$C_3$ alkoxy, $C_3$-$C_6$ cycloalkyl, or with one or more fluoro atom(s); $C_3$-$C_6$ cycloalkyl; $C_2$-$C_6$ alkenyl; or $C_2$-$C_6$ alkynyl,
$R^3$ is H; $C_1$-$C_6$ alkyl optionally substituted with OH, $C_1$-$C_3$ alkoxy, $C_3$-$C_6$ cycloalkyl, or with one or more fluoro atoms; $C_3$-$C_6$ cycloalkyl; $C_2$-$C_6$ alkenyl; or $C_2$-$C_6$ alkynyl,
$R^4$ is $C_1$-$C_6$ alkyl optionally substituted with $C_3$-$C_6$ cycloalkyl or with one or more fluoro atom(s); $C_2$-$C_6$ alkenyl; $C_2$-$C_6$ alkynyl; or $C_3$-$C_6$ cycloalkyl,
$R^5$ is $SO_2NR^6R^7$; $NHSO_2NR^6R^7$; $NHCOCONR^6R^7$; $NHSO_2R^8$; $NHCOR^8$; or phenyl or heterocyclyl either of which is optionally substituted with one or more fluoro atom(s) or $C_1$-$C_3$ alkyl;
$R^6$ and $R^7$ are each independently H or $C_1$-$C_6$ alkyl optionally substituted with OH, $CO_2H$, $C_1$-$C_3$ alkoxy, $C_3$-$C_6$ cycloalkyl, or with one or more fluoro atom(s); or together with the nitrogen atom to which they are attached form either a mono-cyclic ring selected from the group consisting of: imidazole, aziridine, azetidine, pyrrolidine, piperidine, morpholine, piperazine and homopiperazine, or a bicyclic ring selected from the group consisting of 2,5-diazabicyclo[2.2.1]heptane and 3,7-diazabicyclo[3.3.0] octane, wherein said group is optionally substituted with $R^9$,
$R^8$ is $C_1$-$C_3$ alkyl optionally substituted with one or more fluoro atom(s); or $C_3$-$C_7$ cycloalkyl;
$R^9$ is $C_1$-$C_6$ alkyl optionally substituted with one or more halide atom(s), OH, $C_1$-$C_3$ alkoxy which is optionally substituted with one or more fluoro atom(s), $CO_2R^{10}$, $NR^{11}R^{12}$, $C=NR^{13}$ ($NR^{14}R^{15}$), or with a tetrazole group which is optionally substituted with $C_1$-$C_3$ alkyl;

or one or more nitrogen containing heteroaryl group which is optionally substituted with one or more fluoro atom(s), $R^{10}$ is H; or $C_1$-$C_4$ alkyl optionally substituted with OH, $NR^{11}R^{12}$, one or more fluoro atom(s), or with a nitrogen containing heterocyclic ring selected from the group consisting of pyrrolidine, piperidine, piperazine, morpholine, pyrrole, and imidazole wherein nitrogen atom is directly bound to $C_1$-$C_4$ alkyl, $R^{11}$ and $R^{12}$ are each independently H or $C_1$-$C_4$ alkyl, $R^{13}$ is H; $C_1$-$C_4$ alkyl optionally substituted with one or more fluoro atoms; or $C_1$-$C_6$ cycloalkyl, R14 and R15 are each independently H or C1-C4 alkyl optionally substituted with one or more fluoro atoms; C3-C6 cycloalkyl; or together with the nitrogen atom to which they are attached form a pyrrolidinyl, piperidino, morpholino, piperazinyl, or homopiperazinyl group wherein said group is optionally substituted with $C_1$-$C_3$ alkyl.

2. The method of claim 1, wherein the PDE5 inhibitor is at least one selected from the group consisting of:
- 2-(2-ethoxy-5-(4-methyl)piperazin-1-ylsulfonyl)phenyl)-5-methyl-7-n-propyl-3,5-dihydro-4H-pyrrolo[3,2-d]pyrimidin-4-one;
- 2-(5-(4-methylpiperazin-1-ylsulfonyl)-2-n-propoxyphenyl)-5-methyl-7-n-propyl-3,5-dihydro-4H-pyrrolo[3,2-d]pyrimidin-4-one;
- 2-(2-ethoxy-5-(4-n-propylpiperazin-1-ylsulfonyl)phenyl)-5-methyl-7-n-propyl-3,5-dihydro-4H-pyrrolo[3,2-d]pyrimidin-4-one;
- 2-(2-ethoxy-5-(4-isopropylpiperazin-1-ylsulfonyl)phenyl)-5-methyl-7-n-propyl-3,5dihydro-4H-pyrrolo[3,2-d]pyrimidin-4-one;
- 2-(2-ethoxy-5-(4-(2-fluoroethyl)piperazin-1-ylsulfonyl)phenyl)-5-methyl-7-n-propyl-3,5-dihydro-4H-pyrrolo[3,2-d]pyrimidin-4-one;
- 2-(5-(4-(2-fluoroethyl)piperazin-1-ylsulfonyl)-2-n-propoxyphenyl)-5-methyl-7-n-propyl-3,5-dihydro-4H-pyrrolo[3,2-d]pyrimidin-4-one;
- 2-(2-ethoxy-5-(4-(3-fluoropropyl)piperazin-1-ylsulfonyl)phenyl)-5-methyl-7-n-propyl-3,5-dihydro-4H-pyrrolo[3,2-d]pyrimidin-4-one;
- 2-(2-ethoxy-5-(4-(3-fluoropropyl)piperazin-1-ylsulfonyl)phenyl)-7-ethyl-5-methyl -3,5-dihydro-4H-pyrrolo[3,2-d]pyrimidin-4-one;
- 2-(2-ethoxy-5-(4-(3-fluoropropyl)piperazin-1-ylsulfonyl)phenyl)-7-(3-fluoropropyl)-5-methyl-3,5-dihydro-4H-pyrrolo[3,2-d]pyrimidin-4-one;
- 7-cyclopropylmethyl-2-(2-ethoxy-5-(4-(3-fluoropropyl)piperazin-1-ylsulfonyl)phenyl)-5-methyl-3,5-dihydro-4H-pyrrolo[3,2-d]pyrimidin-4-one;
- 2-(2-ethoxy-5-(4-(3-fluoropropyl)piperazin-1-ylsulfonyl)phenyl)-5-ethyl-7-ethyl-3,5-d ihydro-4H-pyrrolo[3,2-d]pyrimidin-4-one;
- 2-(2-ethoxy-5-(4-(3-fluoropropyl)piperazin-1-ylsulfonyl)phenyl)-5-ethyl-7-n-propyl-3,5-dihydro-4H-pyrrolo[3,2-d]pyrimidin-4-one;
- 2-(2-ethoxy-5-(4-isopropylpiperazin-1-ylsulfonyl)phenyl)-5-ethyl-7-n-propyl-3,5-dihydro-4H-pyrrolo[3,2-d]pyrimidin-4-one;
- 2-(2-ethoxy-5-(4-(3-fluoropropyl)piperazin-1-ylsulfonyl)phenyl)-5-ethyl-7-n-propyl-3,5-dihydro-4H-pyrrolo[3,2-d]pyrimidin-4-one;
- 2-(2-ethoxy-5-(4-(2-hydroxyethyl)piperazin-1-ylsulfonyl)phenyl)-5-ethyl-7-n-propyl-3,5-dihydro-4H-pyrrolo[3,2-d]pyrimidin-4-one;
- 2-(2-ethoxy-5-(4-ethylpiperazin-1-ylsulfonyl)phenyl)-5-ethyl-7-(3-fluoropropyl)-3,5-d-ihydro-4H-pyrrolo[3,2-d]pyrimidin-4-one;
- 2-(5-(4-ethylpiperazin-1-ylsulfonyl)-2-n-propoxyphenyl)-5-ethyl-7-(3-fluoropropyl)-3-5-dihydro-4H-pyrrolo[3,2-d]pyrimidin-4-one;
- 2-(2-ethoxy-5-(4-isopropylpiperazin-1-ylsulfonyl)phenyl)-5-ethyl-7-(3-fluoropropyl)-3,5-dihydro-4H-pyrrolo[3,2-d]pyrimidin-4-one;
- 2-(2-ethoxy-5-(4-(3-fluoropropyl)piperazin-1-ylsulfonyl)phenyl)-5-ethyl-7-(3-fluoropr opyl)-3,5-dihydro-4H-pyrrolo[3,2-d]pyrimidin-4-one;
- 2-(5-(4-(3-fluoropropyl)piperazin-1-ylsulfonyl)-2-n-propoxyphenyl)-5-ethyl-7-(3-fluoropropyl)-3,5-dihydro-4H-pyrrolo[3,2-d]pyrimidin-4-one;
- 2-(2-ethoxy-5-(4-(2-hydroxyethyl)piperazin-1-ylsulfonyl)phenyl)-5-ethyl-7-(3-fluoropropyl)-3,5-dihydro-4H-pyrrolo[3,2-d]pyrimidin-4-one;
- 2-(5-(4-(2-hydroxyethyl)piperazin-1-ylsulfonyl)-2-n-propoxyphenyl)-5-ethyl-7-(3-fluoropropyl)-3,5-dihydro-4H-pyrrolo[3,2-d]pyrimidin-4-one;
- 2-(5-(4-(3-hydroxypropyl)piperazin-1-ylsulfonyl)-2-n-propoxyphenyl)-5-ethyl-7-(3-fluoropropyl)-3,5-dihydro-4H-pyrrolo[3,2-d]pyrimidin-4-one;
- 2-(5-(4-(2-hydroxyethyl)piperazin-1-ylsulfonyl)-2-n-propoxyphenyl)-5-ethyl-7-n-propyl-3,5-dihydro-4H-pyrrolo[3,2-d]pyrimidin-4-one;
- 2-(5-(4-(3-fluoropropyl)piperazin-1-ylsulfonyl)-2-n-propoxyphenyl)-5-methyl-7-n-propyl-3,5-dihydro-4H-pyrrolo[3,2-d]pyrimidin-4-one;
- 2-(2-ethoxy-5-(4-(2-hydroxyethyl)piperazin-1-ylsulfonyl)phenyl)-5-methyl-7-n-propyl-3,5-dihydro-4H-pyrrolo[3,2-d]pyrimidin-4-one;
- 2-(5-(4-(2-hydroxyethyl)piperazin-1-ylsulfonyl)-2-n-propoxyphenyl)-5-methyl-7-n-propyl-3,5-dihydro-4H-pyrrolo[3,2-d]pyrimidin-4-one;
- 2-(5-(2-ethoxy-4-(3-hydroxypropyl)piperazin-1-ylsulfonyl)phenyl)-5-methyl-7-n-propyl-3,5-dihydro-4H-pyrrolo[3,2-d]pyrimidin-4-one;
- 2-(5-(4-(3-hydroxypropyl)piperazin-1-ylsulfonyl)-2-n-propoxyphenyl)-5-methyl-7-n-propyl-3,5-dihydro-4H-pyrrolo[3,2-d]pyrimidin-4-one;
- 2-(2-ethoxy-5-(4-(hydroxycarbonylmethyl)piperidin-1-ylsulfonyl)phenyl)-5-methyl-7-n-propyl-3,5-dihydro-4H-pyrrolo[3,2-d]pyrimidin-4-one;
- 2-(5-(4-(hydroxycarbonylmethyl)piperidin-1-ylsulfonyl)-2-n-propoxyphenyl)-5-methyl-7-n-propyl-3,5-dihydro-4H-pyrrolo[3,2-d]pyrimidin-4-one;
- 2-(2-ethoxy-5-(4-(2-hydroxycarbonylethyl)piperidin-1-ylsulfonyl)phenyl)-5-methyl-7-n-propyl-3,5-dihydro-4H-pyrrolo[3,2-d]pyrimidin-4-one;
- 2-(5-(4-(2-hydroxycarbonylethyl)piperidin-1-ylsulfonyl)-2-n-propoxyphenyl)-5-methyl-7-n-propyl-3,5-dihydro-4H-pyrrolo[3,2-d]pyrimidin-4-one;
- 2-(2-ethoxy-5-(4-(1H-tetrazol-5-ylmethyl)piperazin-1-ylsulfonyl)phenyl)-5-methyl -7-n-propyl-3,5-dihydro-4H-pyrrolo[3,2-d]pyrimidin-4-one;
- 5-methyl-2-(2-n-propoxy-5-(4-(2-(1H-tetrazol-5-yl)ethyl)piperazin-1-ylsulfonyl)phenyl)-7-n-propyl-3,5-dihydro-4H-pyrrolo[3,2-d]pyrimidin-4-one;
- 2-(2-ethoxy-5-(4-(1H-tetrazol-5-ylmethyl)piperidin-1-ylsulfonyl)phenyl)-5-methyl-7-n-propyl-3,5-dihydro-4H-pyrrolo[3,2-d]pyrimidin-4-one;
- 5-methyl-2-(2-n-propoxy-5-(4-(1H-tetrazol-5ylmethyl)piperidin-1-ylsulfonyl)phenyl)-7-n-propyl-3,5-dihydro-4H-pyrrolo[3,2-d]pyrimidin-4-one;

and pharmaceutically acceptable salts, solvates, and hydrates thereof.

3. The method of claim 2, wherein the PDE5 inhibitor is mirodenafil, or a pharmaceutically acceptable salt, solvate or hydrate.

\* \* \* \* \*